United States Patent [19]

Rourke

[11] Patent Number: 5,797,858
[45] Date of Patent: Aug. 25, 1998

[54] SPOOLING PULLBACK FOR CATHETER IMAGING AND THERAPY CORES

[75] Inventor: Jonathan M. Rourke, Belmont, Mass.

[73] Assignee: Hewlett-Packard Company, Palo Alto, Calif.

[21] Appl. No.: 818,026

[22] Filed: Mar. 14, 1997

[51] Int. Cl.$^6$ ............................................. A61B 5/00
[52] U.S. Cl. .................... 600/585; 600/433; 600/434; 604/96; 604/282
[58] Field of Search ........................ 600/585, 433, 600/434, 435; 604/95, 96, 280, 281, 282

[56] References Cited

U.S. PATENT DOCUMENTS

| | | | |
|---|---|---|---|
| 4,397,091 | 8/1983 | Gustavsson et al. | 600/434 |
| 4,917,094 | 4/1990 | Lynch et al. | 600/434 |
| 5,185,004 | 2/1993 | Lasninski | 600/434 |
| 5,361,768 | 11/1994 | Webler et al. | |
| 5,562,619 | 10/1996 | Mirarchi et al. | 604/282 |

*Primary Examiner*—Max Hindenburg
*Assistant Examiner*—Pamela L. Wingood

[57] ABSTRACT

A pullback device for axial positioning of a core of an intravascular catheter, including a pullback chassis having a catheter extension extending therefrom for attachment of the intravascular sheath with a distal passage therethrough and an interface unit extension for attachment of an interface unit with a proximal passage therethrough. An intermediate sheath receives and encloses the intravascular catheter drive cable and has a pullback loop for enclosing the drive cable. The pullback loop includes a fixed segment attached to the proximal passage through the interface unit extension and a variable segment extending towards the distal end of the intravascular sheath and having a sliding section adjoining the distal end of the intravascular sheath. When the catheter is attached to the device, the catheter drive cable extends from the proximate end of the intravascular catheter and through the distal passage, the intermediate sheath and the proximal passage for connection to the interface unit wherein the drive cable forms a loop contained within the intermediate sheath pullback loop forming a loop between the distal and proximal passages. The intermediate sheath is attached to an attachment point of an actuating member and the actuating member acts to increase and decrease the length of the sliding section of the variable segment included in the pullback loop, thereby enlarging and reducing the diameter of the pullback loop and the length of drive cable contained in the pullback loop to control the axial location of the working head.

24 Claims, 3 Drawing Sheets

5,797,858

SPOOLING PULLBACK FOR CATHETER IMAGING AND THERAPY CORES

FIELD OF THE INVENTION

The present invention relates to intravascular ultrasound imaging and therapy catheters and, in particular, to a spooling pullback for manual and motorized axial positioning of catheter imaging and therapy cores.

BACKGROUND OF THE INVENTION

Intravascular ultrasound imaging and therapy catheters are commonly used in many medical applications, such as the acquisition of images of the heart and the blood vessels, and for medical procedures on the heart and blood vessels, such as dilating occluded arteries.

Intravascular catheters are typically comprised of a tubular intravascular sheath and a core that includes a working head located at the distal end of the catheter and a drive cable running through the intravascular sheath to a proximal end of the catheter sheath and providing various tubular electrical and mechanical connections to the working head. The working head may be comprised, for example, of a diagnostic imaging device, such as an ultrasonic transducer for obtaining ultrasound images, or a therapy tool such as an angioplasty "balloon" or a rotational cutting or grinding tool for removing plaque from the blood vessel, or a combination of such elements, and may be enclosed wholly or partially within the distal end section of the catheter or may protrude entirely from the distal end of the catheter.

In typical use, and in example, a diagnostic imaging catheter is introduced into a blood vessel at a convenient point, usually through an inductor sheath, and is passed through the blood vessel until the transducer is located in the region of interest, such as near the heart or in a section of artery that is to be examined. The working head may then be rotated and moved axially within the intravascular sheath by the drive cable, for example, to successively position an ultrasonic transducer to obtain images at locations along the intravascular sheath within a predetermined range of axial movement, typically about six inches. In a similar fashion, the drive cables are used to advance a therapeutic cutting or grinding tool into rotating contact with successive sections of a plaque deposit to be removed and, in other applications, a drive cable may be used to position an angioplasty balloon in an occluded artery for subsequent inflation.

The proximal end of the drive cable is typically connected to an interface unit that provides electrical and mechanical connections as required to devices that control the axial and rotational movement of the working head or the operations of the working head, or both. For example, the working head of an ultrasonic imaging intravascular catheter is comprised of an ultrasonic transducer to transmit and receive ultrasonic signals and use of the imaging catheter requires that the transducer be both positioned axially with respect to the distal end of the intravascular sheath, to select a region to be scanned, and rotated to scan the region of interest. This, in turn, requires that the drive cable and the interface unit provide both electrical connections to the electronics of an ultrasound imaging system and mechanical connections to manual or motorized devices for controlling the axial and rotational positions and movement of the transducer. Yet other intravascular catheters, such as balloon angioplasty catheters or catheters having cutting or grinding heads for removal of plaque from an artery will often require only mechanical connections through the drive cable and the interface unit to manual or motorized devices for controlling the axial position and rotational movement of the working head, or to couple pressurized fluids for balloon inflation.

In a typical intravascular catheter, the axial position and movement of the working head with respect to the distal end of the intravascular sheath is controlled by withdrawing or inserting the drive cable from or into the intravascular sheath, thereby moving the working head a like distance with respect to the distal end of the intravascular sheath. Rotational position and movement of the working head is typically controlled by rotation of the drive cable. In this regard, it should be noted that the movement of the working head along the intravascular sheath is generally referred to as "pullback" because ultrasonic imaging is usually performed with a withdrawing motion of the transducer working head. Contemporary designs, however, facilitate both "forward" and pullback movement as the region of interest is often scanned several times in imaging applications while the removal of plaque often requires several passes with the removal tool, as may the positioning of an angioplasty balloon and the placement of "stents" to hold open an artery.

It is therefore apparent that the operation and uses of an intravascular catheter imposes certain design requirements upon the catheter assembly. For example, and as described, in typical usage the catheter is inserted into a blood vessel, such as an artery, until the distal end of the intravascular sheath is located in or near the region of interest and the working head is then translated axially and rotated with respect to the intravascular sheath by axial movement and rotation of the drive cable relative to the intravascular sheath as necessary to carry out the intended procedure. The axial positioning and rotation of the working head with respect to the intravascular sheath, in turn, however, requires that the drive cable be controllably movable in both the axial and rotational directions with respect to the intravascular sheath. This, in turn, requires that the intravascular sheath be coupled or mounted to a structure or member that is stationary with respect to the subject, and that the drive cable, and thus the transducer, be coupled or mounted to a structure or member that is axially and rotationally moveable with respect to the intravascular sheath. The drive cable, however, must be mechanically or electrically connected to the interface unit, or both, so that the interface unit in turn must be mounted or coupled to axially and rotationally move with the drive cable, and thus with respect to the intravascular sheath and its mounting.

The problem may be further compounded in that some intravascular catheters also include a flush port and connection through fluids may be passed through the intravascular sheath to the distal portion of the catheter. Such fluids include, for example, a saline solution to surround a transducer head to provide acoustic coupling to surrounding tissues and radioflorescent dyes or ultrasound contrast agents to be injected into the region of interest for radiolucent or ultrasound imaging of the region.

Typical solutions of the prior art to this design problem are shown, for example, in U.S. Pat. No. 5,361,768 to Webler et al. for an AUTOMATED LONGITUDINAL POSITION TRANSLATOR FOR ULTRASONIC IMAGING PROBES, AND METHODS OF USING SAME. In the implementation of an intravascular ultrasound catheter shown therein, the proximal end of the intravascular sheath is mechanically connected to a housing while the proximal end of the drive cable connecting to the probe transducer is mechanically and electrically connected to a probe drive module. The probe drive module in turn, is movably mounted in the housing and includes a drive unit, also movably mounted in the housing, which contains the mechanical components, such as gears and couplings, for rotating the drive cable and thus probe transducer, and electrical components for electrically connecting the drive cable wires from the probe transducer to an ultrasound transceiver. The housing also contains a linear translation module that is mechanically coupled to the probe drive housing and includes the mechanical components, such as gears and couplings, for controlling the axial movement of the drive cable and thus the axial position of the transducer probe. While the rotational and linear motions of the probe transducer can be manually controlled through, respectively, the probe drive module and the linear translation module, the probe drive module and the linear translation module are driven by motors mounted on a separate structure and connected to the probe drive module and the linear translation module by drive shafts. In other systems, the rotational and axial motors are mounted, respectively, in the probe drive housing and in the linear translation module or in the housing.

It can therefore be seen from the examples presented in U.S. Pat. No. 5,361,768 that there many inherent problems in the designs of the prior art. For example, it is apparent in the designs of the prior art that only certain components of the assembly are mechanically stationary with respect to the bedside or examination table during movement of the image core, and that the interface unit and the probe drive module and the linear translation module, and most probably the housing, will move relative to the bedside or examination table during any motion of the image core. These relatively large moving assemblies create ergonomic and logistical difficulties, particularly since the available working space, and the sterile field in which the procedure is taking place, are constrained and shared with personnel and other instruments and devices.

It is also apparent that these relatively large moving assemblies can result in variable mechanical loads and forces being applied to the inductor sheath through which the intravascular ultrasound catheter is introduced into the subject, resulting in discomfort and possible injury to the subject. It is further apparent that there is a significant risk of accidental movement of these assemblies, with a consequential risk of inadvertent and unwanted movement of the intravascular sheath or working head and injury to the subject.

It is also apparent that these problems are significantly increased when the pullback device is motorized because of the additional weight and volume of the motorization devices, drive trains, control and power wires and controls, particularly if the motorized pullback device is to provide a clinically useful range of axial movement of the working head, commonly referred to as the "pullback distance" and typically approximately six inches.

It is also apparent that manual movement of the transducer requires the use of two hands, one to hold the intravascular sheath stationary and one to retract, advance or rotate the drive cable and interface unit, thus effectively requiring the full efforts and attention of a clinician in an already crowded workspace.

In addition, the size and weight of both manual and motorized pullback devices of the prior art has resulted in the devices being constructed as separate units from the catheter and interface units, with the pullback devices, motors and so forth being introduced into the sterile field in their own sterile bags and assembled to the to the catheter and interface unit for each procedure. The alternative, constructing the pullback device, the catheter and the interface unit as a single assembly, results in a large, complex and expensive device that is awkward and expensive to use.

The present invention therefore provides a solution to these and other problems of the prior art by providing an improved pullback device.

SUMMARY OF THE INVENTION

The present invention is directed to a pullback device for axial positioning of a core of an intravascular catheter, the intravascular catheter including an intravascular sheath and a core wherein the core includes a working head located at a distal end of the intravascular sheath and a drive cable running through the intravascular sheath to a proximal end of the intravascular sheath. The distal end of the catheter core may be either contained within the sheath at all times, or exposed as in the case of a therapy core.

According to the present invention, the pullback device includes a pullback chassis having a catheter extension extending therefrom for attachment of the proximal end of the intravascular sheath with a distal passage therethrough and an interface unit extension extending therefrom for attachment of the interface unit with a proximal passage therethrough.

An intermediate sheath receives and encloses the intravascular catheter drive cable and has a pullback loop for enclosing the drive cable wherein the pullback loop includes a fixed segment attached to the proximal passage through the interface unit extension and a variable segment extending along the drive cable towards the distal end of the intravascular sheath and having a sliding section adjoining the distal end of the intravascular sheath. When the catheter is attached to the device, the catheter drive cable extends from the proximate end of the intravascular catheter and through the distal passage, the intermediate sheath and the proximal passage for connection to the interface unit wherein the drive cable forms a loop contained within the intermediate sheath pullback loop forming a loop between the distal and proximal passages.

The device further includes actuating member wherein the intermediate sheath is attached to an attachment point of the actuating member at the junction between the fixed and variable segments of the intermediate sheath. According to the present invention, the actuating member acts to increase and decrease the length of the sliding section of the variable segment included in the pullback loop, thereby enlarging and reducing the diameter of the pullback loop and the length of drive cable contained in the pullback loop to thereby control the axial location of the working head with respect to the distal end of the intravascular sheath.

In a present embodiment, the actuating member is a rotating element pivoted in the pullback chassis and the attachment point is located on a circumferential point of the rotating element. In a presently preferred embodiment, the rotating element is a generally flat element, such as a plate, forming at least a segment of a circle and pivoted on a center point of a diameter of the rotating element and the rotating element includes a circumferential groove in an outer face of the rotating element for receiving and constraining the sliding portion of the variable segment of the intermediate sheath.

The pullback chassis also preferably includes a generally circular rim wall and a back wall forming a loop chamber for enclosing the pullback loop and the actuating member and the actuating member is a rotating element pivoted in the back wall of the pullback chassis, wherein the attachment point is located on a circumferential point of the rotating element and the rotating element rotates about a central point of the back wall. In this embodiment, the rotating element is again a generally flat element forming at least a segment of a circle and pivoted on a center point of a diameter of the semi-circular element and the element includes a circumferential groove in an outer face of the rotating element for receiving and constraining the sliding portion of the variable segment of the intermediate sheath.

Further according to the present invention, the pullback device includes a telescoping section extending from the proximate end of intravascular sheath and having an interior diameter and length for receiving the sliding section of the intermediate sheath and, in a preferred embodiment, the telescoping section is formed by a portion of the distal end of the intravascular sheath having an enlarged interior diameter.

The pullback device may also include a generally circular bearing mounted in the distal passage of the catheter extension for supporting the intermediate sheath. The catheter extension may further include a flush port opening extending from the exterior of the catheter extension and into the distal passage between the generally circular bearing for the passage of fluids from the flush port and along the interior of the intravascular sheath towards the distal end of the intravascular sheath and the generally circular bearing also acts as a fluid seal to prevent the flow of fluid towards the pullback loop.

Finally, the pullback device may be constructed and provided as a complete assembly together with the intravascular catheter, so that only the interface unit need be attached to the pullback device before the pullback device and catheter are ready for use.

Other features, objects and advantages of the present invention will be understood by those of ordinary skill in the art after reading the following descriptions of a present implementation of the present invention, and after examining the drawings, wherein:

DESCRIPTION OF PREFERRED EMBODIMENTS OF THE INVENTION

Referring to FIGS. 1, 2 3, and 4, therein are shown a diagrammic front and side views, in part in cross section, of an embodiment of the intravascular catheter Pullback Device 10 according to the present invention. It will be noted that FIGS. 1 through 4 are not drawn to scale or in relative proportion, but are drawn to most clearly show and describe an embodiment of the present invention, and that typical dimensions of an exemplary embodiment are discussed in the following description.

A. Structure of Pullback Device 10

Figure 1:
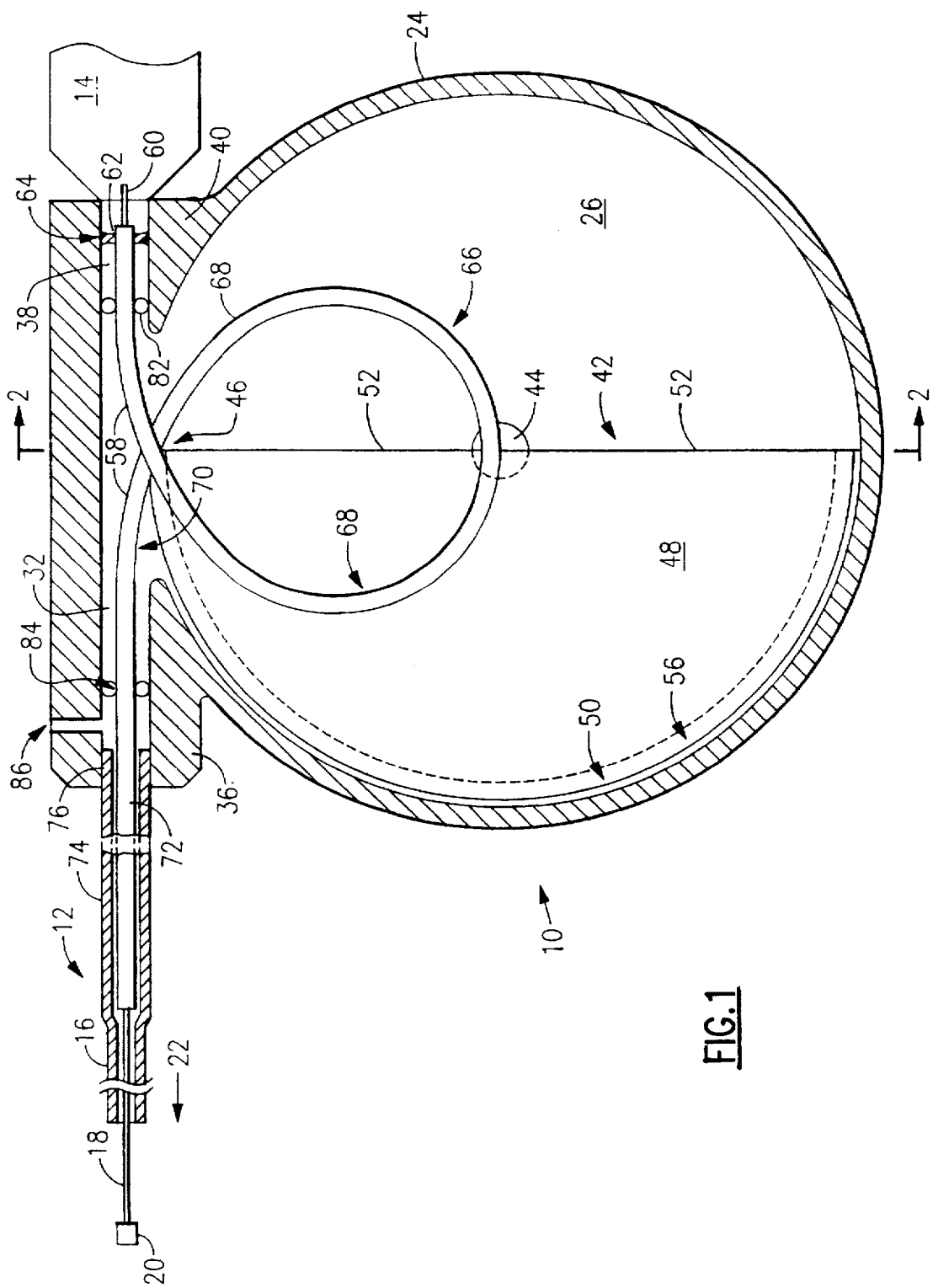
FIG. 1 is diagrammic front view, in part in cross section, of a pullback device of the present invention.

As shown in FIG. 1, Pullback Device 10 is connected between an Intravascular Catheter 12 and an Interface Unit 14 wherein Intravascular Catheter 12 is comprised of an Intravascular Sheath 16 and a Drive Cable 18 providing the electrical and mechanical connections necessary for a particular type of Work Head 20 located at Intravascular Distal End 22 of Intravascular Catheter 12, as described herein above and as well understood in the relevant arts. Interface Unit 14, in turn, contains, for example, the mechanical components necessary for rotation of Drive Cable 18 to control the rotational position and movement of Work Head 20 and the electrical connections necessary to connect the wiring of Drive Cable 18 to, for example, an ultrasound imaging system or other medical electronic system, or therapy device such as a rotational cutter, also as described herein above and as well understood in the relevant arts.

In a typical embodiment of Pullback Device 10, such as for an ultrasound imaging catheter and which will be used for purposes of example and illustration of the present invention in the following discussions, Intravascular Catheter 12 may be approximately 40 inches long and the interior and exterior diameters of Intravascular Sheath 16 may be, respectively, 0.033 and 0.040 inch, while Drive Cable 18 may be 0.029 inch in diameter. Intravascular Sheath 16 is typically comprised of polystyrene while Drive Cable 18 is of a specialized multilayer, multifiber stainless steel and polyethylene construction.

In the presently preferred embodiment of a Pullback Device 10 for an ultrasound imaging catheter illustrated herein, Pullback Device 10 includes a Pullback Chassis 24 having a generally circular well-like Loop Chamber 26 formed by a circular Back Wall 28 of Pullback Chassis 24 having a Rim Wall 30 extending upwards around the circumference of Back Wall 28. In the exemplary embodiment described herein, Loop Chamber would typically have a diameter of 3 inches and Back Wall 28 would have a thickness of 0.125 inch while Rim Wall 30 may be 0.125 inch high and 0.25 inch thick. Pullback Chassis 24 may typically be comprised of polycarbonate or nylon and may be cast or machined.

A Distal Passage 32 extends generally tangentially from the inner circumference of Rim Wall 30 at Inner Side 34 of Rim Wall 30 and through Rim Wall 30 and a Catheter Extension 36 of Pullback Chassis 24 extending towards Intravascular Catheter 12.

A Proximal Passage 38 similarly extends tangentially from the inner circumference of Rim Wall 30 at Inner Side 34 of Rim Wall 30 and through Rim Wall 30 and an Interface Unit Extension 40 of Pullback Chassis 24 extending towards Interface Unit 14.

In the presently preferred embodiment of a Pullback Device 10 for an ultrasound imaging catheter illustrated herein, Proximal Passage 38 and Distal Passage 32 may be drilled or cast in Pullback Chassis 24.

As will be discussed further below, Catheter Extension 36 is designed to mate and connect with the proximate end of Intravascular Catheter 12, and in particular with Intravascular Sheath 16, while Interface Unit Extension 40 is designed to mate and connect with Interface Unit 14 and, in particular, to facilitate the necessary electrical and mechanical connections between Drive Cable 18 and Interface Unit 14, dependent upon the functions of a particular Intravascular Catheter 12 that is connected to Pullback Device 10 and Interface Unit 14. In this regard, Interface Unit Extension 40 will mechanically mate with Interface Unit 14 so that Interface Unit 14 is constrained from lateral or rotational movement with respect to Pullback Device 10 when Interface Unit 14 is mated with Interface Unit Extension 40. As is well understood and commonly practiced in the art, this may be accomplished by shaping the mating end of Interface Unit Extension 40 to engage with a locking coupling device or mechanism comprising part of Interface Unit 14, or by a locking coupling device or mechanism in or on the mating end of Interface Unit Extension 40 that is designed to engage with Interface Unit 14.

Figure 2:
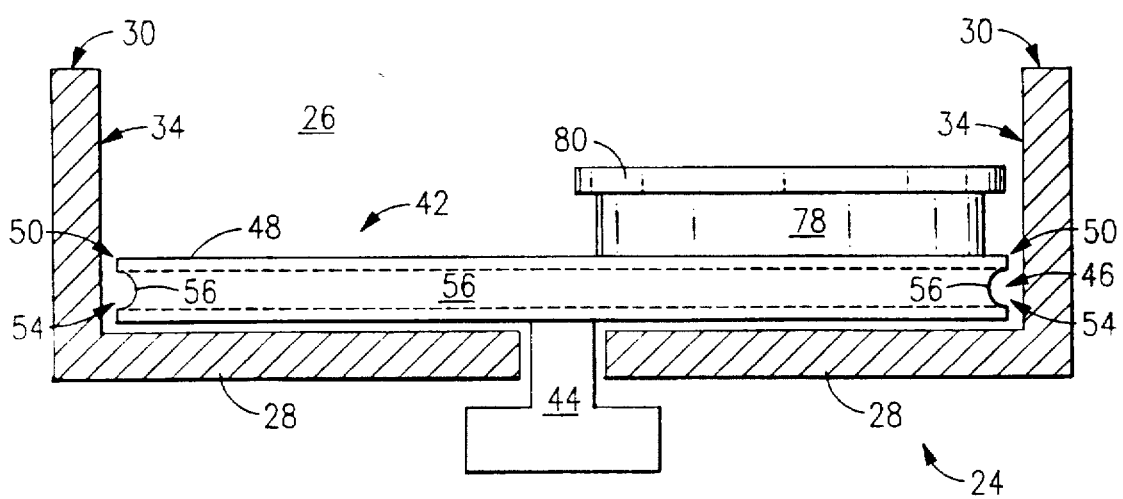
FIG. 2 is a partial diagrammic side view, in part in cross section, of a pullback device of the present invention.

Pullback Device 10 further includes a Actuating Mechanism 42 which rotates about a Axis 44 located in the center of Back Wall 28 and extends from Axis 44 to an Attachment Point 46 adjacent Inner Side 34 of Rim Wall 30. In a presently preferred embodiment, as illustrated in FIGS. 1 and 2, wherein FIG. 2 is a partial side view of Pullback Device 10 along the section line A—A of FIG. 1, Actuating Mechanism 42 includes an Actuating Member 48 having the shape of a generally semi-circular plate having a Circumferential Edge 50 adjacent and paralleling Inner Side 34 of Rim Wall 30. As shown, Attachment Point 46 is located at one end of Circumferential Edge 50 and a straight Chord Edge 52 extends from Attachment Point 46 on Circumferential Edge 50 and through an Axis 46 located at Axis 44 to Circumferential Edge 50 at a point generally diametrically opposite Attachment Point 46. It will be noted that the representation of Pullback Device 10 shown in FIG. 2 has been simplified in the area of Distal Passage 32 and Proximal Passage 38 for clarity of illustration of Actuating Member 48 and that the structure of these areas of Pullback Device 10 are shown more fully in FIGS. 1, 3 and 4.

In the presently preferred embodiment of a Pullback Device 10 for an ultrasound imaging catheter illustrated herein, Actuating Member 48 may have, for example, a diameter of approximately 4 inches and a thickness of approximately 0.25 inch and may be cast or machined of nylon.

As also shown in FIGS. 1 and 2, Outer Face 54 of Circumferential Edge 50, that is, the edge of Actuating Member 48 facing and parallel to Inner Side 34 of Rim Wall 30, is provided with a Groove 56 which runs along Outer Face 54 from Attachment Point 46 to the diametrically opposite point on Circumferential Edge 50. It will also be noted that, as shown in FIG. 2, Attachment Point 46 is located essentially in Groove 56 at the junction between Circumferential Edge 50 and Chord Edge 52.

As discussed further below, Groove 56 is of a width and depth to closely accommodate Drive Cable 18 and an intermediate sheath enclosing Drive Cable 18, and the distance or separation clearance between Outer Face 54 and Inner Side 34 is such to allow free rotation of Actuating Member 48 while insuring that Drive Cable 18 and the intermediate sheath enclosing Drive Cable 18 will be trapped and retained in Groove 56. It will also be noted from FIG. 2 that Actuating Member 48 is positioned adjacent to Back Wall 28 and sufficiently close to Back Wall 28 to prevent Drive Cable 18 and its enclosing intermediate sheath from being trapped between Actuating Member 48 and Back Wall 28 while allowing free rotation of Actuating Member 48 and, for example, may be in sliding contact with Back Wall 28.

In the presently preferred embodiment of a Pullback Device 10 for an ultrasound imaging catheter illustrated herein, Groove 56 may have a width of approximately 0.080 inch and a depth of approximately 0.125 inch and the space between Outer Face 54 and Inner Side 34 may be approximately 0.020 inch while the separation between Back Wall 28 and Actuating Member 48 may be approximately 0.010 inch.

Lastly, Pullback Device 10 includes an Intermediate Sheath 58 which closely encloses Drive Cable 18 such that Drive Cable 18 is free to rotate within Intermediate Sheath 58, but without side to side play, movement or vibration within Intermediate Sheath 58. In the presently preferred embodiment of a Pullback Device 10 for an ultrasound imaging catheter illustrated herein, Intermediate Sheath 58 may be comprised, for example, of nylon and have a circular cross section with an exterior diameter of 0.062 inch and an interior diameter of 0.036 inch.

As shown in FIG. 1, a Cable Proximal End 60 of Drive Cable 18 extends from a Intermediate Proximal End 62 of Intermediate Sheath 58 to engage with Interface Unit 14 and is provided with mechanical and electrical connections as necessary to mechanically and electrically mate and connect with Interface Unit 14. As is well known and commonly practiced in the art, the connection between Drive Cable 18 and Interface Unit 14 may be required to rotate in certain applications while the connection may be non-rotating in certain other applications. As such, the design of this interconnection will depend upon the specific application and type of Intravascular Catheter 12 and in certain applications may require mating electrical and/or mechanical couplers attached or connected or mounted to Cable Proximal End 60 and Interface Unit 14 while other applications may require only a coupler in Interface Unit 14 that engages with Drive Cable 18.

As illustrated in FIG. 1, the Cable Proximal End 60 that mates and engages with Intermediate Proximal End 62 is, in turn, mechanically attached to Interface Unit Extension 40 at an Anchor Point 64 at or within Proximal Passage 38, for example, near Interface Unit 14, so as to be restrained from rotational or axial movement with respect to Pullback Chassis 24. Intermediate Proximal End 62 may be attached to Interface Unit Extension 40, for example, by adhesive, a friction fit, a flanged coupling, or any of the suitable attachment methods well known to those or ordinary skill in the relevant arts.

Intermediate Sheath 58 and enclosed Drive Cable 18 then extend from their respective attachment points at Anchor Point 64 and Interface Unit 14 and through Proximal Passage 38 and into Loop Chamber 26, wherein Intermediate Sheath 58 and enclosed Drive Cable 18 are formed into a Pullback Loop 66 before continuing into Distal Passage 32. As indicated in FIG. 1, the length of Intermediate Sheath 58 forming Pullback Loop 66 is divided into a Fixed Segment 68 extending from Attachment Point 46 to the entry point of Pullback Loop 66 into Proximal Passage 38 and a Variable Segment 70 extending from Attachment Point 46 to the entry point of Pullback Loop 66 into Distal Passage 32. As also generally illustrated in FIG. 1, and as will be further apparent in a following discussion of a FIG. 3, Pullback Loop 66 is located in Loop Chamber 26 and Intermediate Sheath 58 is mechanically attached to Actuating Member 48 at Attachment Point 46, for example, by adhesive, so that Intermediate Sheath 58 is restrained from axial or rotational movement with respect to Actuating Member 48.

In this regard, and for purposes a subsequent discussion of the operation of Pullback Device 10, it will be noted that Actuating Member 48 is shown in FIG. 1 as rotated into the fully counter-clockwise position, also referred to hereafter as the 0° position or the full extension position, wherein Working Head 20 is position at the furthest extension with respect to Intravascular Sheath 16. In this position, Pullback Loop 66 is largely comprised of Fixed Segment 68, that is, the length of Intermediate Sheath 58 with enclosed Drive Cable 18, extending from Proximal Passage 38 to Attachment Point 46 as, in this position of Actuating Member 48, Attachment Point 46 is located near or adjacent to the entry point of Distal Passage 32 and Variable Segment 70 is, as a consequence, of relatively short length.

Before continuing with the present description, it will be noted that in this and the following descriptions the device of the present invention may be constructed and operated in the mirror image reverse from what is described herein, and with yet other, similar variations from the implementation described herein, without departing from the invention as described herein. It will be apparent to those of ordinary skill in the relevant arts, moreover, that such alternate implementations are the full functional and structural equivalents of the implementation described herein and the changes necessary for such variations from the implementation described herein will be obvious to those of ordinary skill in the arts.

Continuing with the description of Intermediate Sheath 58 and enclosed Drive Cable 18, a Sliding Section 72 of Intermediate Sheath 58, together with enclosed Drive Cable 18, extends from Attachment Point 46 and along a line generally tangential to Circumferential Edge 50 and Inner Side 34 of Rim Wall 30 to pass into and through Distal Passage 32 and into an enlarged Telescopic Section 74 of Intravascular Sheath 16. As will be described in the subsequent discussion of the operation of Pullback Device 10, the clockwise rotation of Actuating Member 48 from the 0°, or maximum extension position, will draw an increasing length of Sliding Section 72, together with enclosed Drive Cable 18, into Loop Chamber 26 to become part of the length of Variable Segment 70 therein, so that the length of Variable Segment 70 increases as Actuating Member 48 is rotated in the clockwise direction.

In the presently preferred embodiment of a Pullback Device 10 for an ultrasound imaging catheter illustrated herein, for example, and as discussed further with regard to the operation of Pullback Device 10, the diameter of Actuating Member 48 is approximately 4 inches while the length of Fixed Segment 68 is approximately 6 inches, the length of Variable Segment 70 is approximately 6 inches, and the length of Sliding Section 72 is at least 6 inches.

The interior diameter of Telescopic Section 74 is such as to accept Sliding Section 72 of Intermediate Sheath 58 therein in a sliding fit, but without excess clearance for side to side play, movement or vibration of Intermediate Sheath 58 in Telescopic Section 74, for example, a diameter of approximately 0.090 inch in the exemplary embodiment of an ultrasound imaging catheter discussed herein. Also, and as will be discussed further in the following, the lengths of Telescopic Section 74 and Sliding Section 72 are generally equal to or greater than the desired "pullback distance" of Working Head 20, typically on the order of six inches.

As indicated diagrammatically, Intravascular Sheath Proximate End 76 is attached to Catheter Extension 36, for example, within or at the outer end of Distal Passage 32, so that the internal passage within Telescopic Section 74 is centered and coaxial with Distal Passage 32. As in the attachment of Intermediate Sheath 58 to at Anchor Point 64, Intravascular Sheath Proximate End 76 may be attached to Catheter Extension 36, for example, by adhesive, a friction fit, a flanged coupling, or any of the suitable attachment methods well known to those or ordinary skill in the relevant arts.

B. Operation of Pullback Device 10

Figure 3:
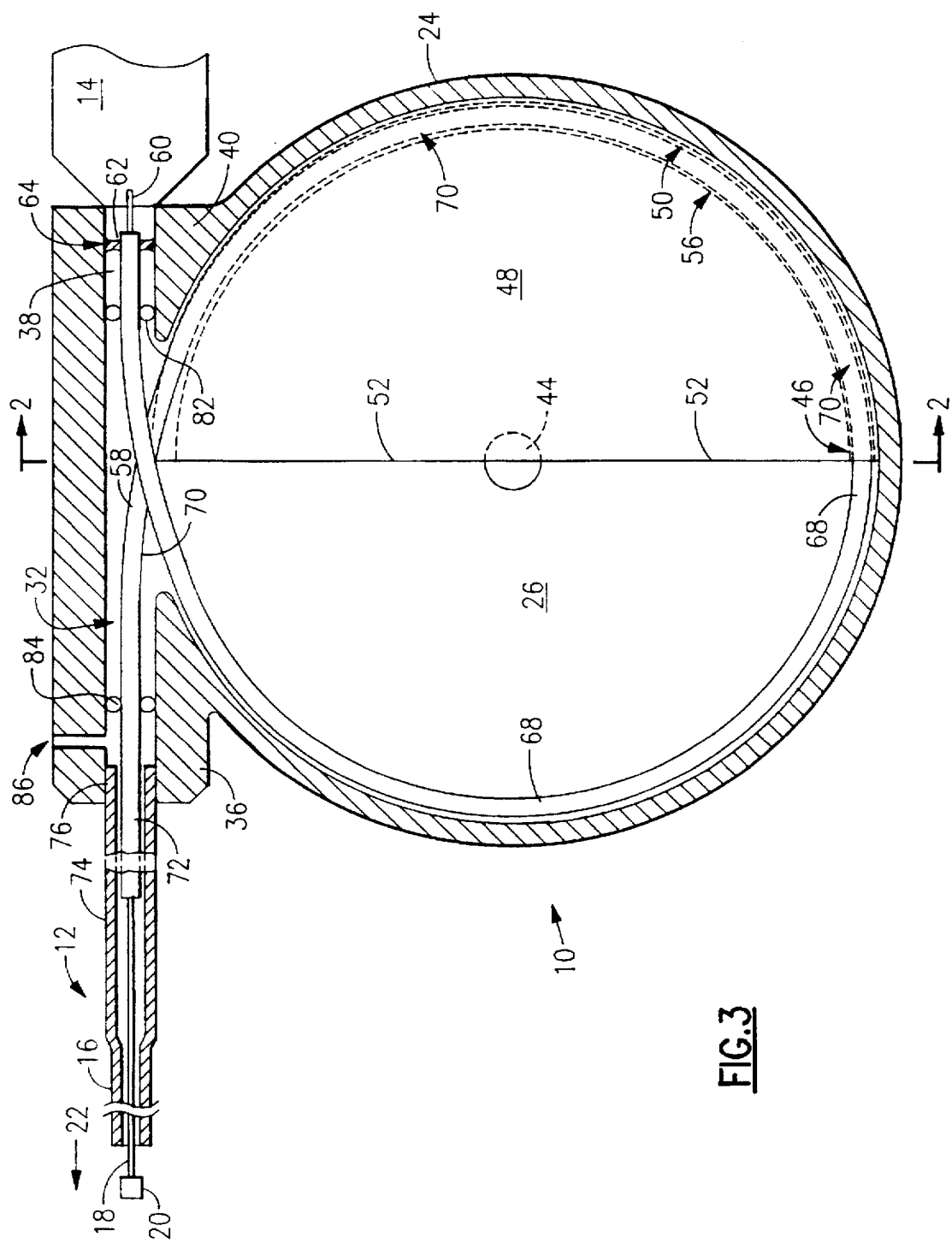
FIG. 3 is second diagrammic front view, in part in cross section, of a pullback device of the present invention; and, FIG. 4 is a second diagrammic side view, in part in cross section, of a pullback device of the present invention.

Now referring to FIGS. 1 and 3 and considering the operation of Pullback Device 10, it has been described above that Intravascular Sheath 16, including Telescopic Section 74 is mechanically connected to Pullback Device 10, and specifically that the proximal end of Telescopic Section 74, that is, Intravascular Sheath Proximate End 76, is attached to Catheter Extension 36. As such, Intravascular Sheath 16 is not free to move with respect to Pullback Chassis 24, either rotationally or axially, and the distance between Intravascular Distal End 22 of Intravascular Catheter and Pullback Chassis 24 is fixed.

It has been also described above that Intermediate Sheath 58 is mechanically attached to Pullback Chassis 24, specifically at Anchor Point 64 in Catheter Extension 36, and is thereby axially and rotationally fixed with respect to Pullback Chassis 24, while Drive Cable 18, which is enclosed within Intermediate Sheath 58, is mechanically attached, and in many applications electrically connected, to Interface Unit 14, which in turn is also mechanically coupled to Catheter Extension 36 of Pullback Chassis 24. As such, and while Drive Cable 18 is free to rotate within Intermediate Sheath 58, by operation of Interface Unit 14, the axial position of Drive Cable 18 within Intermediate Sheath 58 is fixed.

Further considering the relationship between Drive Cable 18 and Intravascular Sheath 16 as established by the above described mechanical structures, it may be seen from the above that the proximal ends of Drive Cable 18 and Intravascular Sheath 16 are in a fixed relationship to one another because both are connected to the rigid structure of Pullback Chassis 24. The distal ends of Drive Cable 18 and Intravascular Sheath 16, that is, at Working Head 20, and at Intravascular Distal End 22 of Intravascular Sheath 16, however, are not fixed with respect to one another. In particular, Working Head 20 is capable of axial motion with respect to Intravascular Distal End 22 because of the sliding coupling between Intravascular Sheath 16 and Intermediate Sheath 58, including the enclosed Drive Cable 18, provided by Telescopic Section 74 of Intravascular Sheath 16 and Sliding Section 72 of Intermediate Sheath 58.

In addition, while the length or distance between Intravascular Distal End 22 of Intravascular Sheath 16 and the attachment point of Drive Cable 18 to Interface Unit 14 is fixed, being essentially comprised of the length of Intravascular Sheath 16 plus the distance across Pullback Chassis 24 to the attachment point of Interface Unit 14, and the length of Drive Cable 18 is fixed, the length of Drive Cable 16 along Intravascular Sheath 16 is not fixed.

In particular, the distance along Drive Cable 18 from Interface Unit 14 to Working Head 20 is comprised of the distance between the attachment of Drive Cable 18 to Interface Unit 14 and the start of Pullback Loop 66, which is fixed, the length of Drive Cable 18 contained in the circumference of Pullback Loop 66, and the length of the portion of Drive Cable 18 extending from the end of Pullback Loop 66 to Working Head 20 along Intravascular Sheath 16. Therefore, while the total length of Drive Cable 18 is fixed, the proportion of that length enclosed in Pullback Loop 66, and thus the proportion of that length along Intravascular Sheath 16 and therefore the axial position of Working Head 20 with respect to Intravascular Distal End 22 of Intravascular Sheath 16, are variable and are determined by the circumference of Pullback Loop 66.

The circumference of Pullback Loop 66 is, in turn, determined by the rotational angle of Actuating Member 48. As described, Intermediate Sheath 58 is attached to Pullback Chassis 24 at Anchor Point 64 and to Actuating Member 48 at Attachment Point 46. Attachment Point 46 follows a circular path of fixed radius about Axis 44 when Actuating Member 48 rotates and, because of the resilience of Intermediate Sheath 58 with enclosed Drive Cable 18, Pullback Loop 66 will retain an approximately circular configuration at all angles of rotation of Attachment Point 46 about Axis 44 while Fixed Segment 68, in turn, defines a circumferential arc of fixed length along the circumference of Pullback Loop 66.

Considering the geometry of Pullback Loop 66, Fixed Segment 68 and Attachment Point 46, it will be apparent that a line from Attachment Point 46 to the point that Pullback Loop 66 enters Proximal Passage 38 approximates a chord of the circle formed by Pullback Loop 66, hereafter referred to as "Chord 46/38", wherein the ends of Chord 46/38 intersect the circumference of the Pullback Loop 66 circle at the ends of the circumferential arc defined by Fixed Segment 68. It will also be apparent that the length of Chord 46/38 is dependent upon the rotational position of Attachment Point 46 about Axis 44; that is, Chord 46/38 will increase and decrease in length as Attachment Point 46 is rotated away or towards Proximal Passage 38. It will be noted that the term "approximates" is used with respect to the circle formed by Pullback Loop 66 and the chord formed by Chord 46/38 because the point at which Pullback Loop 66 enters Proximal Passage 38 does not lie on the circle defined by the motion of Attachment Point 46, although the separation is relatively small.

It is well known and understood in geometry that, given a circle, such as Pullback Loop 66, a circumferential arc of fixed length along the circumference of the circle, such as that defined by Fixed Segment 68, and a chord of the circle connecting the ends of the circumferential arc, such as Chord 46/38, wherein the chord is of variable length, the diameter and circumference of the circle are determined by and a function of the length of the chord. In Pullback Mechanism 10, therefore, the diameter and circumference of Pullback Loop 66 are determined by and functions of the length of Chord 46/38, which in turn is determined by and a function of the rotational position of Attachment Point 46 about Axis 44.

It has been described herein above that the circumference of Pullback Loop 66 is comprised of a fixed portion, that is, Fixed Segment 68, and a variable portion comprised of Variable Segment 70 which, in turn, is comprised of a portion of Sliding Section 72 of Intermediate Sheath 58 that, together with enclosed Drive Cable 18, extends from Attachment Point 46 and through Distal Passage 32 into Telescopic Section 74 of Intravascular Sheath 16. Therefore, and because the length of Fixed Segment 68 is fixed, the portion of the circumference of Pullback Loop 66 that is comprised of Variable Segment 70 is a function of and determined by the circumference of Pullback Loop 66, which in turn is a function of and determined by the length of Chord 46/38, which is a function of and determined by the rotational position of Attachment Point 46 about Axis 44. For example, when Actuating Member 48 is in the 0° rotation position illustrated in FIG. 1, the circumferential arc defined by Fixed Segment 68 subsumes an angle of 360° and Fixed Segment 68 thereby comprises the entire circumference of Pullback Loop 66, which is then at its minimum diameter, so that the circumference of Pullback Loop 66 formed by Variable Segment 70 is essentially zero and the entire length of Sliding Section 72 is contained in Telescopic Section 74. When Actuating Member 48 is rotated clockwise to the 180° rotation position illustrated in FIG. 3, Fixed Segment 68 subsumes an angle of 180° and Fixed Segment 68 comprises one half of the circumference of Pullback Loop 66, which, in the present embodiment, is then at its maximum diameter, so that one half the circumference of Pullback Loop 66 is formed by Variable Segment 70 and a corresponding length of Sliding Section 72 is withdrawn from Telescopic Section 74.

It is apparent, therefore, that the length of Intermediate Sheath 58 residing in Telescopic Section 74 as Sliding Section 72, and the length of Intermediate Sheath 58 comprising Variable Segment 70 of Pullback Loop 66, are determined by and a function of the rotational angle of Actuating Member 48. In a like manner, and while Drive Cable 18 is not connected or attached to Intermediate Sheath 58 and is free to rotate within Intermediate Sheath 58, Drive Cable 18 is enclosed within Intermediate Sheath 58 and thereby is forced to assume the same diameter in Pullback Loop 66 as does that portion of Intermediate Sheath 58 comprising Pullback Loop 66. As such, the length of Drive Cable 18 enclosed in Intermediate Sheath 58 in Telescopic Section 74 in Sliding Section 72, and the length of Drive Cable 18 in Intermediate Sheath 58 comprising Variable Segment 70 of Pullback Loop 66, are likewise determined by and a function of the rotational angle of Actuating Member 48.

Therefore, the length of Drive Cable 18 residing in Sliding Section 72 in Telescopic Section 74 of Intravascular Sheath 16 will decrease or increase, respectively, as the rotational angle of Actuating Member 48 is increased or decreased. In a like manner, and because the length of Drive Cable 18 residing in Telescopic Section 74 of Intravascular Sheath 16 decreases and increases as the rotational angle of Actuating Member 48 is increased or decreased, the axial position of Working Head 20 with respect to Intravascular Distal End 22 of Intravascular Catheter 12 will move towards and away from Pullback Chassis 24 as the rotational angle of Actuating Member 48 is increased or decreased.

It will be apparent, therefore, that the "pullback distance" of Working Head 20 will be determined by the difference in circumference of Pullback Loop 66 from the minimum rotational angle of Actuating Member 48 and the maximum rotational angle of Actuating Member 48. At the minimum rotational angle of Actuating Member 48, the entire circumference of Pullback Loop 66 is essentially comprised of Fixed Segment 68 and the maximum length of Sliding Section 72 resides in Telescopic Section 74 of Intravascular Catheter 12. In this regard, it will be noted that it is necessary for Drive Cable 18 to rotate freely in Intermediate Sheath 58, including the portion of Intermediate Sheath 58 comprising Pullback Loop 66, and without binding, "kinking", vibration or excessive sideways movement. This requirement, in turn, imposes a minimum diameter on Pullback Loop 66; for example, in the present example of an Intravascular Catheter 12 having an ultrasound imaging transducer as Working Head 20, the minimum diameter of Pullback Loop 66 is selected as approximately 2 inches, so that the minimum circumference of Pullback Loop 66, and thus the length of Fixed Segment 68, is approximately 6 inches.

As has been discussed herein above, a typical pullback distance for an Intravascular Catheter 12, such as the ultrasound imaging catheter of the present example, is on the order of six inches, so that the difference in circumference of Pullback Loop 66 from the minimum rotational angle of Actuating Member 48, that is, the minimum circumference of Pullback Loop 66, and the maximum rotational angle of Actuating Member 48, that is, the maximum circumference of Pullback Loop 66, is approximately six inches. Given a minimum Pullback Loop 66 circumference of 6 inches, the maximum circumference of Pullback Loop 66 for the present example would be approximately 12 inches. These dimensions are in accordance with the geometry of the above described embodiment of Pullback Device 10, wherein it was described that at the minimum angle of rotation of Actuating Member 48 the entire circumference of Pullback Loop 66 was comprised of Fixed Segment 68, having a length of 6 inches, and that at the maximum angle of rotation of Actuating Member 48 one half of the circumference of Pullback Loop 66 was comprised of Fixed Segment 68, a length of 6 inches, so that the total circumference of Pullback Loop 66 at the maximum angle of rotation is then approximately 12 inches.

This, in turn, requires that Sliding Section 72 and Telescopic Section 74 each have a length of at least 6 inches, that is, the desired pullback distance. Further in this regard, it is preferable that the length of Telescopic Section 74 be at least equal to the pullback distance so that the entire motion of the distal end of Sliding Section 72 of Intermediate Sheath 58 take place within Telescopic Section 74. As a consequence, the distal end of Sliding Section 72 will not be required to traverse the joint between Telescopic Section 74 and Catheter Extension 36, thereby avoiding the risk of the distal end of Sliding Section 72 "snagging" on the joint and allowing a simpler design of joint.

Referring again to Actuating Member 48, it has been described that Outer Face 54 of Circumferential Edge 50 of Actuating Member 48 is provided with a Groove 56 which runs along Outer Face 54 from Attachment Point 46 to the diametrically opposite point on Circumferential Edge 50 and that Attachment Point 46 is located essentially in Groove 56 at the junction between Circumferential Edge 50 and Chord Edge 52. It has also been described that Groove 56 is of a width and breadth to closely accommodate Drive Cable 18 and Intermediate Sheath 58 enclosing Drive Cable 18, and that the distance or separation clearance between Outer Face 54 and Inner Side 34 is such to allow free rotation of Actuating Member 48 while insuring that Drive Cable 18 and the intermediate sheath enclosing Drive Cable 18 will be trapped and retained in Groove 56.

It is shown in FIG. 3 that as Sliding Section 72 is drawn from Telescopic Section 74 to comprised Variable Segment 70, the portion of Intermediate Sheath 58 and enclosed Drive Cable 18 comprising Variable Segment 70 are captured and constrained in Groove 56 between Groove 56 and Inner Side 34 of Rim Wall 30. The semicircular configuration of Actuating Member 48 and Groove 56 thereby constrain Variable Segment 70 to form a circumferential arc having the diameter of Actuating Member 48 and generally tangential to and continuous with both Telescopic Section 74 and Pullback Loop 66 over the entire maximum possible length of Variable Segment 70. This constraint of Intermediate Sheath 58 and enclosed Drive Cable 18, in turn, insures that the radius of curvature of Variable Segment 70 is large enough for free rotation of Drive Cable 18 and that Intermediate Sheath 58 and enclosed Drive Cable 18 do not "kink" or bind in the region of Variable Segment 70, or during the axial movement of Sliding Section 72 between Telescopic Section 74 and Variable Segment 70 of Pullback Loop 66.

It will be understood, however, that Actuating Member 48 may assume other forms. For example, Actuating Member 48 may be formed as a complete disk, rather than a semi-circular disk. In this instance. Groove 56 will contain a sloping section to allow Intermediate Sheath 58 with enclosed Drive Cable 18 to pass from Groove 56 to the "front" face of Actuating Member 48 to form Pullback Loop 66.

In yet another embodiment of Actuating Member 48, Actuating Member 48 may be reduced to a segment of a circle, such as an arm extending from Axis 44 to Attachment Point 46, relying upon the resilience of Intermediate Sheath 58 with enclosed Drive Cable 18 to cause Intermediate Sheath 58 and enclosed Drive Cable 18 to assume a circular shape and to provide a smooth transition between Sliding Section 72 and Variable Segment 70. In this embodiment, the arm of Actuating Member 48 may, for example, be formed to have a generally double wedge shaped cross section, being thicker along a mid-ridge and thinner along each edge, to aid in prevent Intermediate Sheath 58 from being trapped between Actuating Member 48 and Back Wall 28.

In still other embodiment of Actuating Mechanism 42, Actuating Mechanism 42 need not be comprised of a rotating disk or semicircular plate or a rotating arm, but may be comprised, for example, of a plurality of arms whose outer ends approximate a circular path defining the loop formed by Intermediate Sheath 58, the diameter of which is controlled by a cam mechanism acting upon the arms. In yet other embodiments, Actuating Mechanism 42 may be comprised of an arm mounted on the opposite side of Back Wall 28, that is, on the outside of Loop Chamber 26, and pivoted at Axis 44 with an extension thereto bearing Attachment Point 46 and extending through and sliding in and along a circumferential slot cut through Back Wall 28 adjacent and parallel to the inner side of Rim Wall 30.

In yet other embodiments of Pullback Device 10, Intermediate Sheath 58 may have cross sections other than the circular cross section assumed in the example discussed herein. For example, Intermediate Sheath 58 may have an elliptical or rectangular cross section chosen and designed to cause a preferential direction of curvature of Intermediate Sheath 58, for example, in Pullback Loop 66 and Variable Segment 70, thereby reducing the force required to bend Intermediate Sheath 58 into Pullback Loop 66 and Variable Segment 70 and assuring smoother transitions. A non-symmetric cross section will also reduce the tendency of Intermediate Sheath 58 to twist or bend due to friction with rotating Drive Cable 18.

It will also be noted that the pullback distance provided by Pullback Device 10 may be increased or decreased by altering the relative proportions of Fixed Segment 68, by altering the radius of Actuating Member 48, or by forming Pullback Loop 66 with two or more turns, thereby allowing the maximum angle of rotation of Actuating Member 48 to be increased, for example, to 360°.

It will be noted, however, that the dimensions of the present exemplary embodiment of the invention were chosen to allow a pullback distance in the normally acceptable range of 6 inches while keeping non-uniform rotational distortion within acceptable limits. As is well known in the relevant arts, non-uniform rotational distortion in a device such as an intravascular catheter is the undesired rotational and/or axial motion of the drive cable and working head due to non-linear twisting of the drive cable and undesirable side to side motion or vibration of the drive cable and working head as the drive cable rotates. Non-uniform rotational distortion typically arises from friction between the drive cable and sheath, is increased by bends and turns in the drive cable and sheath, and increases with the length of the drive cable and sheath. As a consequence, the dimensions of a typical embodiment of the present invention, including that described herein, would therefore provide a pullback distance of approximately 6 inches for a Fixed Segment of 6 inches and a Variable Segment of 6 inches with a Pullback Loop 66 having a circumference of 6 to 12 inches. It will be understood by those of ordinary skill in the relevant arts, however, that those dimensions may be increased, for example, by using a thicker drive cable and intravascular sheath, by shortening Intravascular Catheter 12, or by other methods described herein, such as an Intermediate Sheath 58 having a non-uniform cross section, supporting Intermediate Sheath 58 in a Groove 56, and supporting the pullback loop with a pullback boss as described below. It may necessary to decrease those dimensions in certain instances, however, as when it is necessary to use a thinner drive cable and intravascular sheath.

Figure 4:
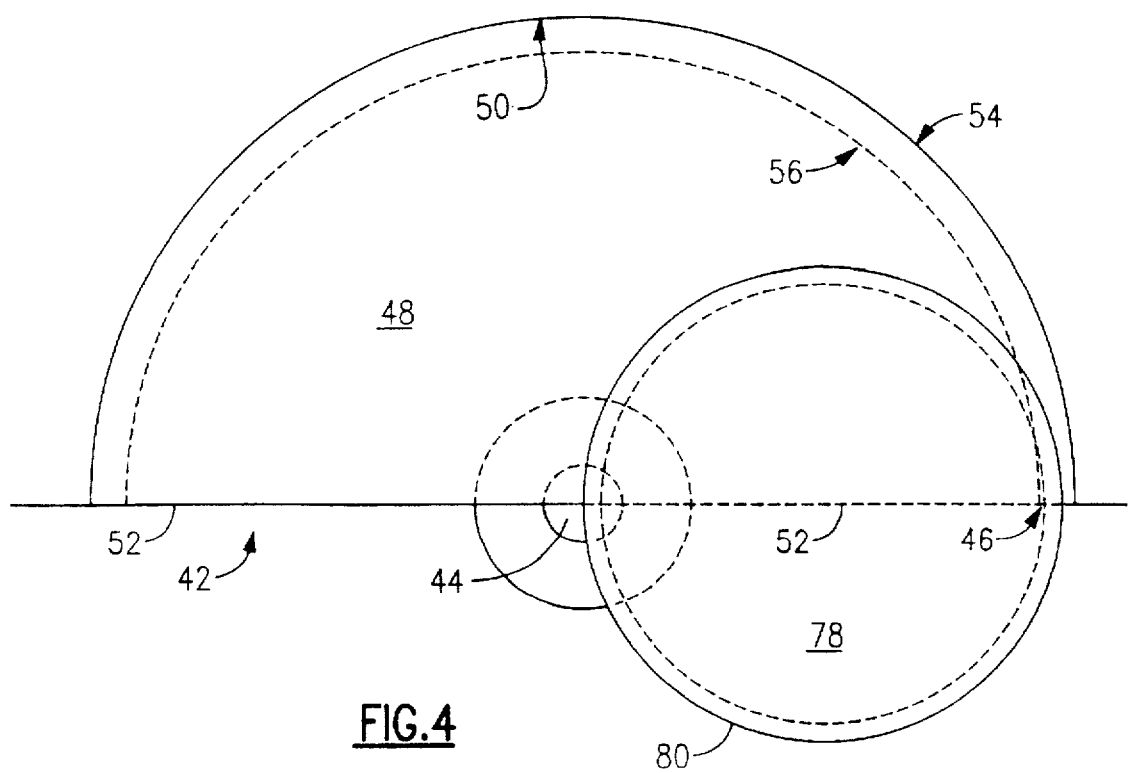

Referring to FIGS. 2 and 4, it is shown therein that Actuating Mechanism 42 may further include a Loop Boss 78 on the "front" face of Actuating Member 48 between Axis 44 and Attachment Point 46 wherein Loop Boss 78 is generally cylindrical with a circumference somewhat smaller than the minimum circumference of Pullback Loop 66, that is, 6 inches in the present example, and is generally made of the same material as Actuating Member 48, being cast as part of Actuating Member 48 or attached as a separate part. As shown, Loop Boss 78 is attached to Actuating Member 48, or molded as part of Actuating Member 48, with the outermost portion of the circumference of Loop Boss 78 near Attachment Point 46 and with Pullback Loop 66 looping around Loop Boss 78. Loop Boss 78 thereby assists in restraining Pullback Loop 66 in a circular form, particularly when Pullback Loop 66 is in the range of its minimum circumference, and assists in aligning Pullback Loop 66 with Distal Passage 32, particularly when the angular rotation of Actuating Member 48 is in the lower range. As also shown in FIGS. 2 and 4, Loop Boss 78 may be provided with a Retaining Cap 80 of diameter greater than Loop Boss 78 to assist in retaining Pullback Loop 66 in position around Loop Boss 78.

As shown in FIGS. 1 and 3, certain implementations of Pullback Device 10 may also be provided with one or more resilient O-Ring Bearings 82 in Proximal Passage 38 wherein an O-Ring Bearing 82 serves to center and support Intermediate Sheath 58 with enclosed Drive Cable in Proximal Passage 38. The provision of an O-Ring Bearing 82 also allows easier manufacture of Pullback Chassis 24 and assembly of Pullback Device 10. In this implementation, Proximal Passage 38 may be cast or drilled to less strict tolerances than if Proximal Passage 38 were to closely fit Intermediate Sheath 58 and Intermediate Sheath 58 with enclosed Drive Cable 18 may be more easily assembled into a larger Proximal Passage 38 as the assembly is guided and supported by O-Ring Bearing 82.

One or more similar resilient O-Ring Bearings 84 may also be provided in Distal Passage 32, for the same reasons, and in this instance an O-Ring Bearing 84 also serves as a sliding bearing surface and guide for the axial motion of Sliding Section 72 between Telescopic Section 74 and Pullback Loop 66.

In the presently preferred embodiment of a Pullback Device 10 for an ultrasound imaging catheter illustrated herein, O-Ring Bearing 82 and 84 may be made of silicone or urethane, and may have an interior diameter of 0.060 inch and an exterior diameter of 0.080 inch.

It has been described herein that in certain applications an Intravascular Catheter 12 may also include a Flush Port 86 located, for example, to intersect Distal Passage 32, and fitted with any of a variety of standard fittings or connectors through which fluids may be passed through Intravascular Sheath 18 to the Distal End 22 of the catheter. Such fluids include, for example, a saline solution to surround a transducer head to provide acoustic coupling to surrounding tissues and radioflorescent dyes or ultrasound contrast agents to be injected into the region of interest for radiolucent or ultrasound imaging of the region. In such embodiments, an O-Ring Bearing 84 also provides a seal between the passage comprised of Flush Port 86, the distal portion of Distal Passage 32 and the interior of Intravascular Sheath 16, and the interior of Pullback Chassis 24, specifically the "upstream" portion of Distal Passage 32 and Loop Chamber 26.

It should also be noted that a Flush Port 86 may also be used, for example, to draw fluids and/or particulate matter, such as plaque ground or cut from an artery, through Catheter 12 and out Flush Port 86, wherein an O-Ring Bearing 84 will also function as a seal, and that an O-Ring Bearing 84 may be designed to provide a gas-tight seal should an application arise requiring the flushing of gases through a Catheter 12.

Next, it will be noted that in FIGS. 1 and 2, for example, Proximal Passage 38 and Distal Passage 32 are shown is essentially aligned across a relatively short chord of Rim Wall 30 of Pullback Chassis 24, and that the openings of Proximal Passage 38 and Distal Passage 32 may be offset to the extent necessary to accommodate the two ends of Pullback Loop 66 so that the two ends of Pullback Loop 66 do not interfere or bind with one another. In other embodiments, the axes of Proximal Passage 38 and Distal Passage 32 may be rotated with respect to one another around Axis 44 so that Proximal Passage 38 and Distal Passage 32 are, for example, at right angles to one another, or parallel, or at any other relative angle to one another, thereby allowing Interface Unit 14 and Intravascular Catheter 12 to be positioned with respect to one another as may be most convenient for a particular application.

Returning to consideration of Actuating Member 48, it is shown in FIG. 2 that Axis 44 may be enlarged on the back side of Back Wall 28, that is, the side opposite Actuating Member 48 and thus accessible to a user of Pullback Device 10, to provide a means for manually rotating Actuating Member 48, thereby allowing the manual control of the axial position of Working Head 20. A suitable scale or distance/rotation indicator may also be provided on the back side of Back Wall 28, to assist a user in positioning Working Head 20. In yet other embodiments, Axis 44 may be provided with a gear mechanism or splined shaft for connection to a motor, so that the location and movement of Working Head 20 can be automatically controlled by an axial position motor, either mounted directly to Pullback Chassis 24 or mounted elsewhere and connected to Axis 44 by a flexible or rigid shaft. Such control might move Working Head 20 at continuous speed, or in an intermittent motion, or in a manner linked to electyrocardiographic data, such as that obtainable through a cardiac ultrasonic imaging system or an EKG monitor, such that the imaging core moves a selected distance on each heart cycle. In this regard, it should be noted that the normal rotational motion of such a motor directly controls the axial position and movement of Drive Cable 18 and Working Head 20 by rotating Actuating Member 48, so that rotational to linear motion devices such as worm gears are not required to actuate the axial motion of Drive Cable 18.

Finally, Pullback Chassis 24 as represented in FIGS. 1 and 2 is open on the "upper" side, that is, the side of Loop Chamber 26 away from Actuating Member 48. In other embodiments, however, Pullback Chassis 24 may be provided with a cover plate over Loop Chamber 26, so that Loop Chamber 26 is completely enclosed.

In yet other alternate embodiments of the present invention, an Intravascular Catheter 12 and an Interface Unit 14 wherein Intravascular Catheter 12 need not be provided with an integral Telescopic Section 74 to accept Sliding Section 72 of Intermediate Sheath 58. Instead, Telescopic Section 74 may be provided by a separate tubular section attached to Intravascular Sheath 16 and having a length and interior diameter equivalent to those of Telescopic Section 74. Alternatively, the interior of Distal Passage 32 may be extended and shaped to form a Telescopic Section 74 with Intravascular Sheath 16 being attached to mate with Distal Passage 32 as described above, so that Distal Passage 32 additional serves the functions performed by Telescopic Section 74. While these alternate embodiments may increase the manufacturing costs of Pullback Device 10, they allow an intravascular catheter manufactured without a Telescopic Section 74 to be used with Pullback Device 10 so long as a sufficient length of Drive Cable 18 is or can be exposed to pass through Intermediate Sheath 58 and to mate with Interface Unit 14.

In conclusion, therefore, the pullback device of the present invention incorporates all functions and requirements of the pullback devices of the prior art into a single, unitary mechanism constructed as a single, unitary structure that is smaller, lighter and less expensive to manufacture than the pullback devices of the prior art. The pullback device of the present invention has no separate or separable moving parts, and can be mounted to a firm structure, such as an operating or examination table. In addition, the pullback device of the present invention offers superior ergonomics, allows single handed operation of the pullback function, and, because the pullback device with an attached intravascular catheter may be assembled and provided as a sterile, packaged assembly, reduces the difficulties in maintaining a sterile operating field as the only additional component necessary to be added to the unit for use is the interface unit. In addition, it is anticipated that the pullback device of the present invention will be assembled together with an intravascular catheter as a single, use disposable device.

Lastly, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. Therefore, it is the object of the appended claims to cover all such variation and modifications of the invention as come within the true spirit and scope of the invention.

What is claimed is:

1. A pullback device for axial positioning of a core of an intravascular catheter, the intravascular catheter including an intravascular sheath and a core wherein the core includes a working head located at a distal end of the intravascular sheath and a drive cable running through the intravascular sheath to a proximal end of the intravascular sheath, comprising:

a pullback chassis having
a catheter extension extending therefrom for attachment of the proximal end of the intravascular sheath with a distal passage therethrough and
an interface unit extension extending therefrom for attachment of the interface unit with a proximal passage therethrough,
an intermediate sheath enclosing the intravascular catheter drive cable and having a pullback loop for receiving and enclosing the the drive cable, the pullback loop including
a fixed segment attached to the proximal passage through the interface unit extension, and
a variable segment extending towards the distal passage and having a sliding section adjoining the distal passage, whereby
when the intravascular catheter is connected to the pullback device the drive cable will extend from the proximate end of the intravascular catheter and through the distal passage, the intermediate sheath pullback loop and the proximal passage for connection to the interface unit, thereby forming a loop between the distal and proximal passages within the intermediate sheath pullback loop, and
an actuating member,
the intermediate sheath being attached to an attachment point of the actuating member at the junction between the fixed and variable segments of the intermediate sheath,
the actuating member acting to increase and decrease the length of the sliding section of the variable segment included in the pullback loop, thereby enlarging and reducing the diameter of the pullback loop and the length of drive cable contained in the pullback loop to thereby control the axial location of the working head with respect to the distal end of the intravascular sheath.

2. The pullback device of claim 1 wherein:
the actuating member is a rotating element pivoted in the pullback chassis and the attachment point is located on a circumferential point of the rotating element.

3. The pullback device of claim 2 wherein:
the rotating element is a generally flat element forming at least a segment of a circle and pivoted on a center point of a diameter of the rotating element.

4. The pullback device of claim 3 wherein the element includes a circumferential groove in an outer face of the rotating element for receiving and constraining the sliding portion of the variable segment of the intermediate sheath.

5. The pullback device of claim 1, wherein the pullback chassis further comprises:
a generally circular rim wall and a back wall forming a loop chamber for enclosing the pullback loop and the actuating member.

6. The pullback device of claim 5 wherein:
the actuating member is a rotating element pivoted in the back wall of the pullback chassis, the attachment point is located on a circumferential point of the rotating element and the rotating element rotates about a central point of the back wall.

7. The pullback device of claim 6 wherein:
the rotating element is a generally flat element forming at least a segment of a circle and pivoted on a center point of a diameter of the rotating element.

8. The pullback device of claim 7 wherein the rotating element includes a circumferential groove in an outer face of the rotating element for receiving and constraining the sliding portion of the variable segment of the intermediate sheath.

9. The pullback device of claim 1, further comprising:
a telescoping section extending from the proximate end of intravascular sheath and having an interior diameter and length for receiving the sliding section of the intermediate sheath.

10. The pullback device of claim 1, wherein the telescoping section is formed by a portion of the distal end of the intravascular sheath having an enlarged interior diameter.

11. The pullback device of claim 1, further including:
a generally circular bearing mounted in the distal passage of the catheter extension for supporting the intermediate sheath.

12. The pullback device of claim 8, wherein the catheter extension further includes a flush port opening extending from the exterior of the catheter extension and into the distal passage between the generally circular bearing for the passage of fluids from the flush port and along the interior of the intravascular sheath towards the distal end of the intravascular sheath, the generally circular bearing acting as a fluid seal to prevent the flow of fluid towards the pullback loop.

13. A pullback device for axial positioning of a core of an intravascular catheter, the intravascular catheter including an intravascular sheath and a core wherein the core includes a working head located at a distal end of the intravascular sheath and a drive cable running through the intravascular sheath to a proximal end of the intravascular sheath, comprising:

a pullback chassis having
 a catheter extension extending therefrom and attached to the proximal end of the intravascular sheath with a distal passage therethrough and
 an interface unit extension extending therefrom for attachment of the interface unit with a proximal passage therethrough, an intermediate sheath enclosing the intravascular catheter drive cable and having a pullback loop for receiving and enclosing the loop of the drive cable, the pullback loop including
 a fixed segment attached to the proximal passage through the interface unit extension, and
 a variable segment extending along the drive cable towards the distal end of the intravascular sheath and having a sliding section adjoining the distal end of the intravascular sheath, whereby
 the drive cable extending from the proximate end of the intravascular catheter and through the distal passage, the intermediate sheath pullback loop and the proximal passage for connection to the interface unit, thereby forming a loop between the distal and proximal passages within the intermediate sheath pullback loop, and an actuating member,
 the intermediate sheath being attached to an attachment point of the actuating member at the junction between the fixed and variable segments of the intermediate sheath,
 the actuating member acting to increase and decrease the length of the sliding section of the variable segment included in the pullback loop, thereby enlarging and reducing the diameter of the pullback loop and the length of drive cable contained in the pullback loop to thereby control the axial location of the working head with respect to the distal end of the intravascular sheath.

14. The pullback device of claim 13 wherein:

the actuating member is a rotating element pivoted in the pullback chassis and the attachment point is located on a circumferential point of the rotating element.

15. The pullback device of claim 14 wherein:

the rotating element is a generally flat element forming at least a segment of a circle and pivoted on a center point of a diameter of the rotating element.

16. The pullback device of claim 15 wherein the rotating element includes a circumferential groove in an outer face of the rotating element for receiving and constraining the sliding portion of the variable segment of the intermediate sheath.

17. The pullback device of claim 13, wherein the pullback chassis further comprises:

a generally circular rim wall and a back wall forming a loop chamber for enclosing the pullback loop and the actuating member.

18. The pullback device of claim 17 wherein:

the actuating member is a rotating element pivoted in the back wall of the pullback chassis, the attachment point is located on a circumferential point of the rotating element and the rotating element rotates about a central point of the back wall.

19. The pullback device of claim 18 wherein:

the rotating element is a generally flat element forming at least a segment of a circle and pivoted on a center point of a diameter of the rotating element.

20. The pullback device of claim 19 wherein the rotating element includes a circumferential groove in an outer face of the rotating element for receiving and constraining the sliding portion of the variable segment of the intermediate sheath.

21. The pullback device of claim 13, further comprising:

a telescoping section extending from the proximate end of intravascular sheath and having an interior diameter and length for receiving the sliding section of the intermediate sheath.

22. The pullback device of claim 13, wherein the telescoping section is formed by a portion of the distal end of the intravascular sheath having an enlarged interior diameter.

23. The pullback device of claim 13, further including:

a generally circular bearing mounted in the distal passage of the catheter extension for supporting the intermediate sheath.

24. The pullback device of claim 23, wherein the catheter extension further includes a flush port opening extending from the exterior of the catheter extension and into the distal passage between the generally circular bearing for the passage of fluids from the flush port and along the interior of the intravascular sheath towards the distal end of the intravascular sheath, the generally circular bearing acting as a fluid seal to prevent the flow of fluid towards the pullback loop.

* * * * *